US011627978B2

(12) United States Patent
Scheltes

(10) Patent No.: US 11,627,978 B2
(45) Date of Patent: Apr. 18, 2023

(54) SURGICAL INSTRUMENT WITH MECHANICALLY OPERABLE LEVER

(71) Applicant: DEAM HOLDING B.V., Groningen (NL)

(72) Inventor: Julien Serge Scheltes, Amsterdam (NL)

(73) Assignee: DEAM HOLDING B.V., Groningen (NL)

( * ) Notice: Subject to any disclaimer, the term of this patent is extended or adjusted under 35 U.S.C. 154(b) by 441 days.

(21) Appl. No.: 16/968,379

(22) PCT Filed: Feb. 7, 2019

(86) PCT No.: PCT/NL2019/050079
§ 371 (c)(1),
(2) Date: Aug. 7, 2020

(87) PCT Pub. No.: WO2019/156559
PCT Pub. Date: Aug. 15, 2019

(65) Prior Publication Data
US 2020/0390462 A1    Dec. 17, 2020

(30) Foreign Application Priority Data
Feb. 12, 2018   (NL) .................................... 2020421

(51) Int. Cl.
*A61B 17/29*   (2006.01)
*A61B 1/005*   (2006.01)
(Continued)

(52) U.S. Cl.
CPC ........ *A61B 17/2909* (2013.01); *A61B 1/0052* (2013.01); *A61B 34/70* (2016.02);
(Continued)

(58) Field of Classification Search
CPC ... A61B 17/2909; A61B 1/0052; A61B 34/70; A61B 2017/00389; A61B 2017/00424;
(Continued)

(56) References Cited

U.S. PATENT DOCUMENTS 4,644,651 A    2/1987  Jacobsen
5,441,494 A *  8/1995  Ortiz .......................... B25J 3/00
                                                            606/1

(Continued)

FOREIGN PATENT DOCUMENTS

WO    2015/029041    3/2015

OTHER PUBLICATIONS

International Search Report for PCT/NL2019/050079 dated Jun. 4, 2019, 5 pages.
(Continued)

*Primary Examiner* — George J Ulsh
(74) *Attorney, Agent, or Firm* — Nixon & Vanderhye

(57) ABSTRACT

A surgical instrument includes a handle with a main body having a central axis, a lever pivotable around a pivot axis fixed with respect to the main body. The lever includes a finger abutment section including a lower finger rest contacting the ventral sides of a user's first and second fingers during pivoting movement of the finger abutment section towards the central axis, and an upper finger rest contacting the dorsal sides of both the fingers during pivoting movement of the finger abutment section away from the central axis; and a septum fixed to lower and upper finger rests and extending therebetween forming a separate first and second finger receiving portion for respectively receiving a first and a second fingers. The lever pivots around the pivot axis such that during pivoting of the lever, the septum central plane remains substantially coplanar with a plane parallel to the central axis.

20 Claims, 8 Drawing Sheets

Figure 1A:
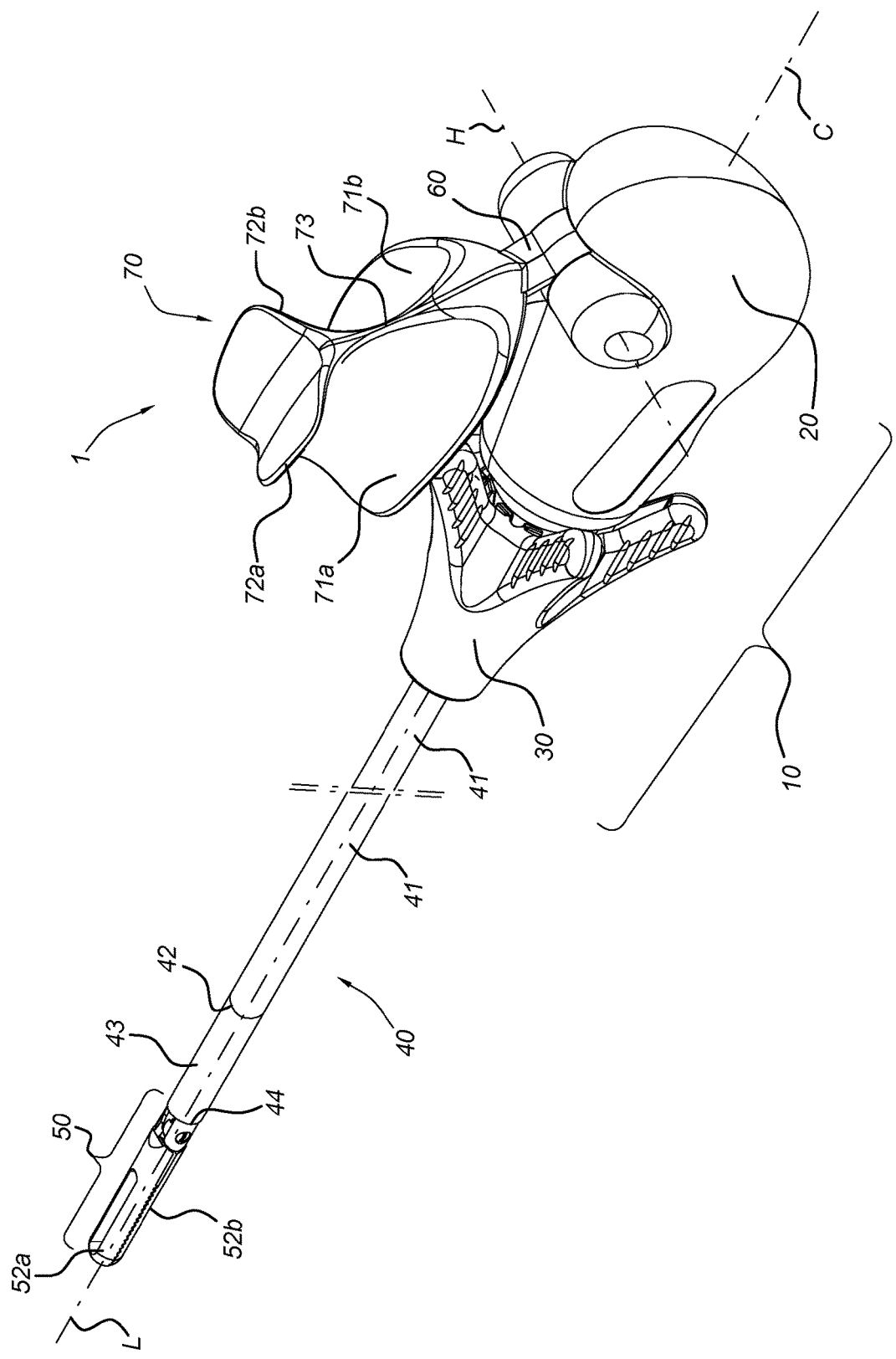

(51) Int. Cl.
*A61B 34/00* (2016.01)
*A61B 17/00* (2006.01)

(52) U.S. Cl.
CPC ..... *A61B 34/76* (2016.02); *A61B 2017/00389* (2013.01); *A61B 2017/00424* (2013.01); *A61B 2017/00438* (2013.01); *A61B 2017/2929* (2013.01)

(58) Field of Classification Search
CPC .. A61B 2017/00438; A61B 2017/2929; A61B 2017/003
See application file for complete search history.

(56) References Cited

U.S. PATENT DOCUMENTS

| | | | |
|---|---|---|---|
| 5,700,275 A | 12/1997 | Bell et al. | |
| 5,797,956 A | 8/1998 | Furnish et al. | |
| 5,976,121 A * | 11/1999 | Matern | A61B 34/71 606/174 |
| 6,666,854 B1 | 12/2003 | Lange | |
| 11,464,594 B2 * | 10/2022 | Lutzow | A61B 34/74 |
| 2002/0103496 A1 | 8/2002 | Harper et al. | |
| 2008/0262538 A1 * | 10/2008 | Danitz | B25J 13/02 606/205 |
| 2013/0331826 A1 * | 12/2013 | Steege | A61B 34/70 606/1 |
| 2016/0113637 A1 | 4/2016 | Abri et al. | |
| 2017/0095236 A1 * | 4/2017 | Sharma | A61B 17/00 |
| 2017/0325903 A1 * | 11/2017 | Nichogi | A61B 18/1445 |
| 2018/0085108 A1 * | 3/2018 | Rimer | A61B 17/068 |
| 2018/0280048 A1 * | 10/2018 | Scheltes | A61B 34/71 |
| 2021/0038865 A1 * | 2/2021 | Sharma | A61B 17/062 |
| 2021/0244427 A1 * | 8/2021 | Lee | A61B 17/29 |

OTHER PUBLICATIONS

Written Opinion of the ISA for PCT/NL2019/050079 dated Jun. 4, 2019, 5 pages.

* cited by examiner

SURGICAL INSTRUMENT WITH MECHANICALLY OPERABLE LEVER

This application is the U.S. national phase of International Application No. PCT/NL2019/050079 filed Feb. 7, 2019 which designated the U.S. and claims priority to NL Patent Application No. 2020421 filed Feb. 12, 2018, the entire contents of each of which are hereby incorporated by reference.

FIELD OF THE INVENTION

The present invention relates to a surgical instrument, such as a endoscopic grasper, comprising: a handle having a main body with a central axis; a tubular body extending from the handle; and a distal tool provided at a distal end of the tubular body away from the handle; wherein a lever is pivotably attached to the main body and is mechanically operable by a user's fingers for mechanically actuating the distal tool, the lever being pivotable about a pivot axis substantially normal to the central axis and having a finger abutment section with a finger receiving portion for receiving a finger of the user. The invention in particular relates to such an instrument in which the force for actuating the distal tool and/or for driving movement thereof is completely and manually provided by the user. Such a surgical instrument in which actuation of the distal tool is powered by the user's hand that holds the surgical instrument provides useful tactile feedback to the user.

BACKGROUND ART

U.S. Patent application US 2016/0113637 describes a surgical instrument with a manual control device for actuation with a hand, wherein the control device can be displaced between a closed position and an opened position. The known control device has a finger lever with a first point of articulation and a second point of articulation, a central element with a third point of articulation and a fourth point of articulation, a connecting lever, which is pivotably arranged at the first point of articulation and at the third point of articulation, and a thumb lever, which is pivotably arranged at the second point of articulation and at the fourth point of articulation. Although the finger lever, the connecting lever and the thumb lever, pivot about points of articulation, i.e. actually move on a circular path, at the same time two or more of the points of articulation are displaced, so that, at least during a phase of the opening process, the distal end of the finger lever is displaced along an at least approximately linear path. This allows the finger lever to slide somewhat along its longitudinal direction towards the central element when the finger lever is operated by a user and while the user's palm rests against a palm rest of the surgical instrument.

Another hand-held surgical instrument is known from U.S. Pat. No. 5,797,956, which comprises a surgical tool and a handle that is provided with a lever, wherein the lever can be closed to activate the surgical tool and is biased to an open position by a spring.

Typically, a working portion provided with a distal tool, such as a gripper, extends from the central element. When the finger lever is actuated, it moves relative to the central element and may thus cause undesirable movement of the central element and of the distal tool attached to the central element, relative to a patient. Moreover, the control device limits the manner in which the distal tool can conveniently be positioned and held. For instance, the separation between a user's thumb and fingers, and/or between the user's fingers, when holding the device is relatively large, which may cause the user's hand to cramp up when holding the device for prolonged periods of time.

It is an object of the invention to provide a surgical instrument that allows a more intuitive and convenient positioning of the distal tool and handle relative to a patient.

It is a further object of the invention to provide a more ergonomical surgical instrument.

SUMMARY OF THE INVENTION

To this end, the present invention provides a surgical instrument comprising: a handle having a main body with a central axis; a tubular body having a main portion extending from the handle and a distal end remote from the handle; a distal tool, provided at the distal end of the tubular body; a lever pivotably attached to the main body and operable by a user's fingers for mechanically actuating the distal tool, the lever being pivotable relative to the main body about a pivot axis substantially normal to the central axis, the lever having a finger abutment section, wherein the finger abutment section comprises a lower finger rest, an upper finger rest and a septum fixed to the lower and upper finger rest and extending therebetween to form a separate first and second finger receiving portion for respectively receiving a first and a second finger of the user, wherein the lower finger rest is adapted for at least partially contacting the ventral sides of both the first and second finger during pivoting movement of said finger abutment section towards the central axis, and wherein the upper finger rest is adapted for at least partially contacting the dorsal sides of both said fingers during pivoting movement of the finger abutment section away from the central axis, wherein the septum has a central plane, wherein a first abutment surface of the septum is arranged on a first side of said plane and adapted for abutting a lateral side of a portion of the first finger of the user's hand in the first finger receiving portion, and wherein a second abutment surface of the septum is arranged on an oppositely facing second side of said plane and adapted for abutting a lateral side of a portion of the second finger of said hand at the same time, wherein the pivot axis is fixed with respect to the main body and wherein the lever is arranged for pivoting around the pivot axis in such a manner that during pivoting of the lever the central plane of the septum remains substantially coplanar with a plane parallel to the central axis. The central plane of the septum preferably extends through the central axis of the handle.

The finger abutment section is adapted for receiving two fingers, e.g. a user's forefinger and middle finger, and actuation of the distal tool may be effected by moving the two fingers, and thus the lever, towards or away from the central axis of the main body, for instance respectively by bending or stretching the two fingers. During such movement of the two fingers, the position the user's thumb and/or other fingers of the same hand may remain substantially unchanged on the handle. The user can thus focus on the force exerted by/on the two fingers in a single direction, rather than having to divide his attention between two oppositely directed forces exerted on thumb and forefinger as known from the prior art. The simple actuation by means of only a single lever facilitates interpretation of tactile feedback from the distal tool. The hand holding the instrument may stay relatively relaxed during use of the instrument, in particular as the grip with which the instrument is held can easily be changed as the only requirement is that both the lever and the main body of the handle can be held by the hand at the same time. The surgical instrument thus provides a greater freedom in placement of the thumb or other fingers on the surgical instrument for gripping the instrument and actuating the distal tool, and in particulars movement of the two fingers relative to the thumb is not as constrained to movement within substantially a single plane.

As the pivot axis around which the lever rotates is fixed with respect to the main body of the handle, movement of the lever relative to the main body is highly predictable, thus providing an intuitive manner of mechanically actuating the distal tool. In particular, due to the pivot axis being fixed, translation of the finger abutment section relative to the main body is substantially prevented.

In an embodiment, when viewed in projection onto the central plane of the septum, the surface of the lower finger rest for contacting the ventral sides of the fingers extends over a first length of at least 2 cm, preferably at least 4 cm and wherein the upper finger rest extends over a second length of between 1 cm and 4 cm, preferably between 2 and 3 cm. The second length of the upper finger rest preferably is smaller than the first length of the lower finger rest. Due to the relatively large distance between the point where the fingers can exert force on the finger abutment section and the hinge axis, a large lever arm is provided. This reduces strain on the fingers when maintaining a strong hold on the instrument, both when the distal tool is being actuated and when the distal tool is not being actuated.

When viewed in projection onto a plane normal to the central plane, a distance between the distal ends of the upper and lower finger rest is substantially smaller than a distance between proximal ends of the upper and lower finger rest, with the distal ends being the ends spaced further apart from the hinge axis than the proximal ends.

Preferably, contacting surface is a substantially convexly curved surface, wherein more preferably said surface when projected onto the central plane, substantially corresponds to a segment of an ellipse having a first diameter in the range of 15 and 21 cm, and a second diameter in the range of 23 cm and 29 cm.

In an embodiment the finger abutment section of the lever is arranged outside of the main body, wherein the lever further comprises a portion arranged within the main body of the handle, wherein said lever portion is connected to the distal tool by means of a mechanical link, e.g. comprising one or more cables and/or push rods, which extends at least partially through the tubular body. Actuation of the distal tool can thus be effected via the mechanical link. Preferably the mechanical link comprises one or more rods or cables, e.g. push rods or Bowden cables, extending from the distal tool to within the main body of the handle, wherein said one or more rods or cables are linked to the lever portion in such a manner that pivoting movement of the lever relative to the handle causes the distal tool to be mechanically actuated. For instance, in case the distal tool is a gripper or cutter, moving the finger abutment section of the lever towards the central axis may cause the gripper or cutter to close, and moving the finger abutment section away from the central axis may cause the gripper or cutter to open.

In an embodiment the handle is provided with a user operable rotation control that is rotatably connected to the main body and fixed to the tubular body in such a manner that rotation of the user operable rotation control relative to the main body causes a corresponding rotation of the tubular body. The user operable control may have a central axis parallel to the longitudinal axis of the tubular body, wherein the user operable control is rotatable around its central axis relative to the main body of the handle. In case the lever portion is connected to the distal tool via a mechanical link, the user operable control is typically arranged to surrounds at least a portion of this link. Preferably the distal tool is rotation fixedly connected to the distal end of the tubular body in such a manner that rotation of the tubular body relative to the main body of the handle causes the distal tool to rotate in conjunction with the tubular body.

In an embodiment the distal end of the tubular body is adapted for bending relative to the main portion of the tubular body, wherein the handle is provided with a user operable bending control adapted for bending relative to the main body of the handle to mechanically cause bending of the distal tool relative to the distal end of the tubular body. The user operable bending control thus allows control of the bending plane and/or a degree of bending of the distal end of the tubular body relative to the main portion of the tubular body.

In a preferred embodiment, the user operable rotation control and the user operable bending control together form a unitary user operable control that is rotatable and bendable relative to the main body of the handle. The user operable rotation and bending control are adapted to be operated by the same hand of a user which holds the main body of the handle. The unitary user operable control is preferably arranged such that when a user holds the main body with one hand and has two fingers resting on the finger abutment portion, the other fingers and/or the user's thumb can reach drive rotation of the user control for rotating the tubular body, and/or can drive bending of the user operable control relative to the main body to drive a corresponding bending of the distal tip of the tubular body relative to the main portion of the tubular body.

In an embodiment, the user operable rotation control partially surrounds an end of the main body, wherein the user operable rotation control, when seen in cross-section through a plane normal to its central axis, has a substantially star-shaped contour, wherein the outer points of the star shape are sufficiently spaced apart from each other and from the inner points of the star shape, for receiving a portion of a user's finger between adjacent points. For instance, the star-shape may have an outer radius in a range of between 2 and 5 cm, and smaller inner radius, e.g. in the rage between 1 and 2 cm. The star-shape preferably is a 5 pointed star shape, though 3,4 or 6 pointed star shapes may be used instead.

In an embodiment a portion of the user operable rotation control that is fixed to the tubular body is arranged between the tubular body and the main body of the handle, and wherein the user operable rotation control has an outer surface arranged in such a manner relative to the finger abutment section and the main body of the handle as to enable a user holding the main body and having one or two fingers in the finger receiving portions to rotate the user operable control around its central axis by moving the outer surface relative to the main body. For instance, a user holding the main body of the instrument while resting two fingers on the finger abutment section, may reach over or past the main body and/or finger abutment section with his thumb and/or other fingers of the same hand to move the rotation control relative to the main body.

Preferably, the main body has a length in the range of 5 to 7 cm,

In an embodiment each of the finger receiving portions is adapted for allowing the user to move his finger into and out of the finger receiving portion in a direction substantially normal to the central plane of the septum. For moving one or both fingers out of their receiving portions each finger may be moved in a direction away from the septum, in particular away from the central plane of the septum. For example, the forefinger and middle finger may move between a position in which they are substantially parallel to each other and contact the septum, to a position in which the fingers are spaced apart from the septum and form a V-shape. Likewise, in order to insert one or both fingers into its receiving portion, each finger may be moved in a direction normal to and towards the septum until a lateral side of each of the fingers abuts the septum. This allows the user to quickly and easily place his fingers into and out of the finger receiving portions when comparted to prior art in which the fingers are to be inserted into rings or loops in a direction of the central axis of such a ring or loop. Preferably, each of the finger receiving portions is open ended at a side thereof opposite from the septum, and more preferably, when seen in cross-section through a plane normal to the central plane of the septum, the finger abutment section has a substantially H-shaped contour.

In an embodiment the main body and the finger abutment section together are adapted for being held in a one-handed pincer-grip, preferably in which the central axis intersects the hand palm of said hand. Such a pincer grip, which preferably is a three-fingered pincer-grip, in which the two fingers may be used to operate the lever while the handle is held by the user between the two fingers in the finger receiving portions and the user's thumb which lies against the handle on a side substantially opposite from the finger abutment section. In case the user moves his two fingers out of the first and second finger receiving portions, he may continue to hold the handle, using fingers and thumb of the same hand.

In an embodiment the lower finger rest comprises a first portion for contacting the ventral side of the first finger and a second portion for contacting the ventral side of the second finger, the upper finger rest comprises a first portion for contacting the dorsal side of the first finger and a second portion for contacting the dorsal side of the second finger, the first portions of the upper finger rest and the lower finger rest face each other and a distance between said portions is in the range of 1.5 to 3 cm, and wherein the second portions of the upper finger rest and the lower finger rest face each other and a distance between said portions is in the range of 1.5 to 3 cm. These dimensions allow a user to comfortably rest his or her fingers on the lower finger rests, while also allowing convenient positioning of the fingers into and out of the finger receiving portions.

In an embodiment the lower finger rest, when seen in projection onto a plane normal to the central plane of the septum, completely overlaps the upper finger rest. For instance, the lower finger rest may have a length of 3.5 cm or more, and the upper finger rest may have a length of 2.5 cm or less in the direction in which the fingers extend during use of the instrument.

In an embodiment, when seen in projection onto the central plane of the septum, the lower finger rest is spaced apart from the upper finger rest by at least 1.5 cm.

In an embodiment, the width of the septum at its thinnest portion is in the range of 1.5-3 mm, and preferably is 2 mm. Even in case the septum extends over a relatively long length, the lateral sides of the adjacent fingers in the first and second finger receiving portions may thus remain close together. Strain on the fingers is thus minimized.

In a preferred embodiment, the main portion of the tubular body is substantially rigid. The distal end of the tubular body may be bendable in case the surgical instrument is provided with a user operable bending control, or may also be rigid, in case no such control is provided.

In an embodiment the lever arcs over an angle of at least 50 degrees when viewed in cross-section through the central plane. Preferably, the lever arcs over such an angle from the hinge axis to a distal end of the finger abutment section.

In an embodiment the lever is movable with respect to the handle between an open and a closed position, wherein the lever is not biased to the open position nor to the closed position. The user thus does not have to exert a force on the lower finger rest or the upper finger rest to keep lever in a same position with respect to the handle, while the lower and upper finger rest enable a user to move the lever between the closed position to the open position. Preferably, when the lever is in the closed position, the finger abutment section is at a first distance from the central axis, and when the lever is in the open position the finger abutment section is at a second distance from the central axis, which second distance is greater than the first distance.

In an embodiment the distal tool comprises a cutter, a gripper and/or a manipulator, that is to be mechanically actuated by means of the lever.

SHORT DESCRIPTION OF DRAWINGS

Figure 1B:
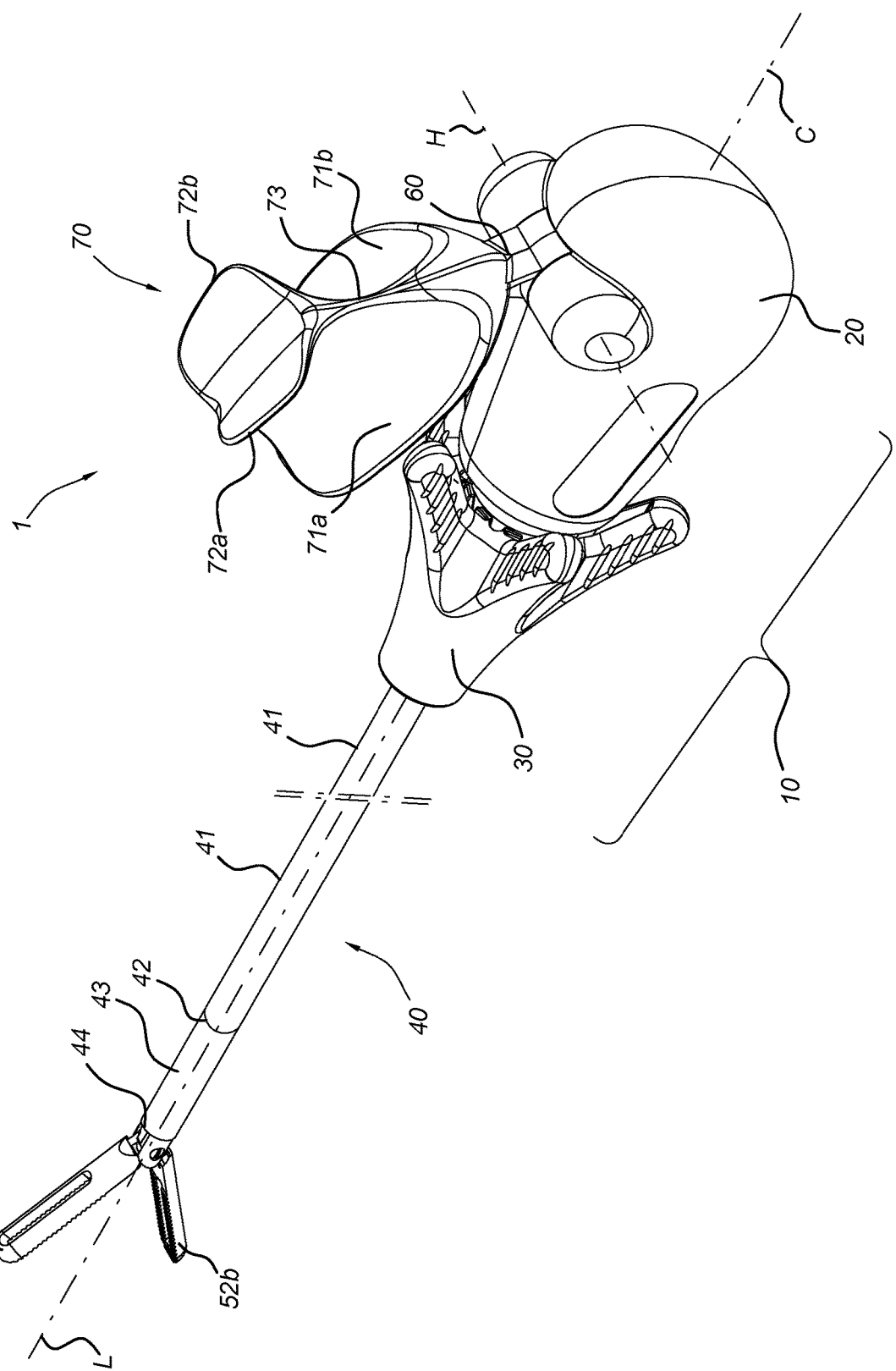
Figure 2:
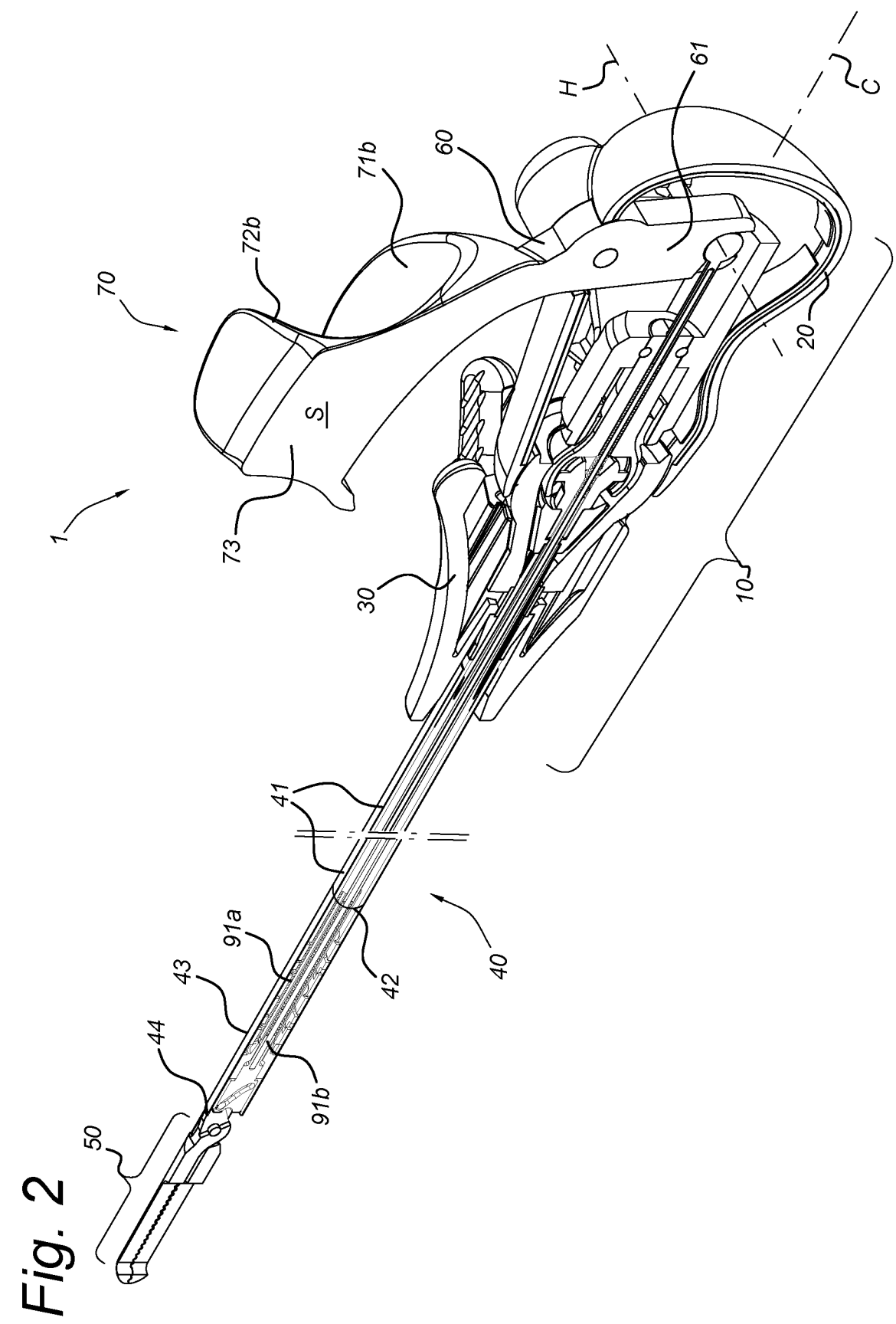
Figure 3A:
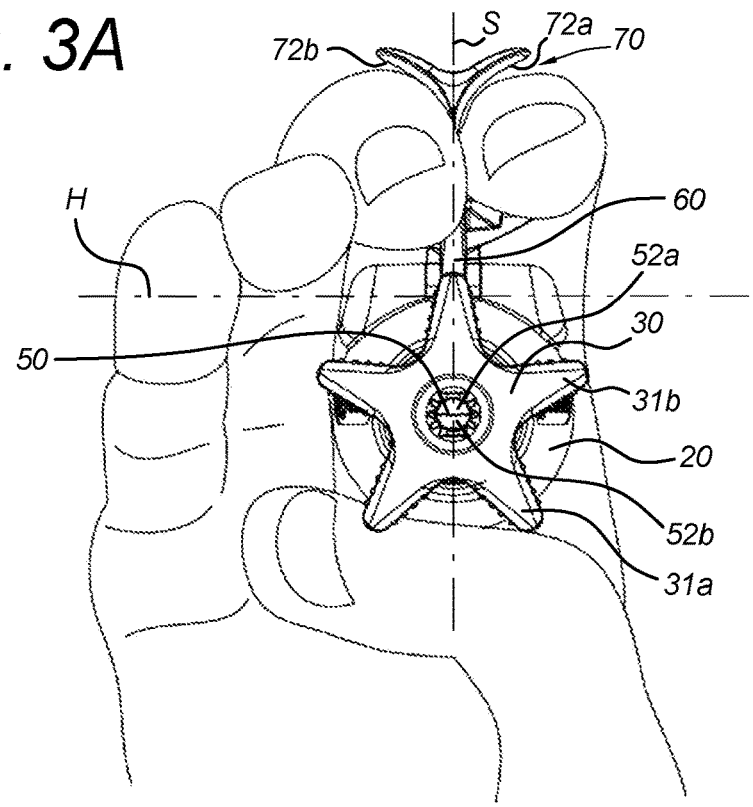
Figure 3B:
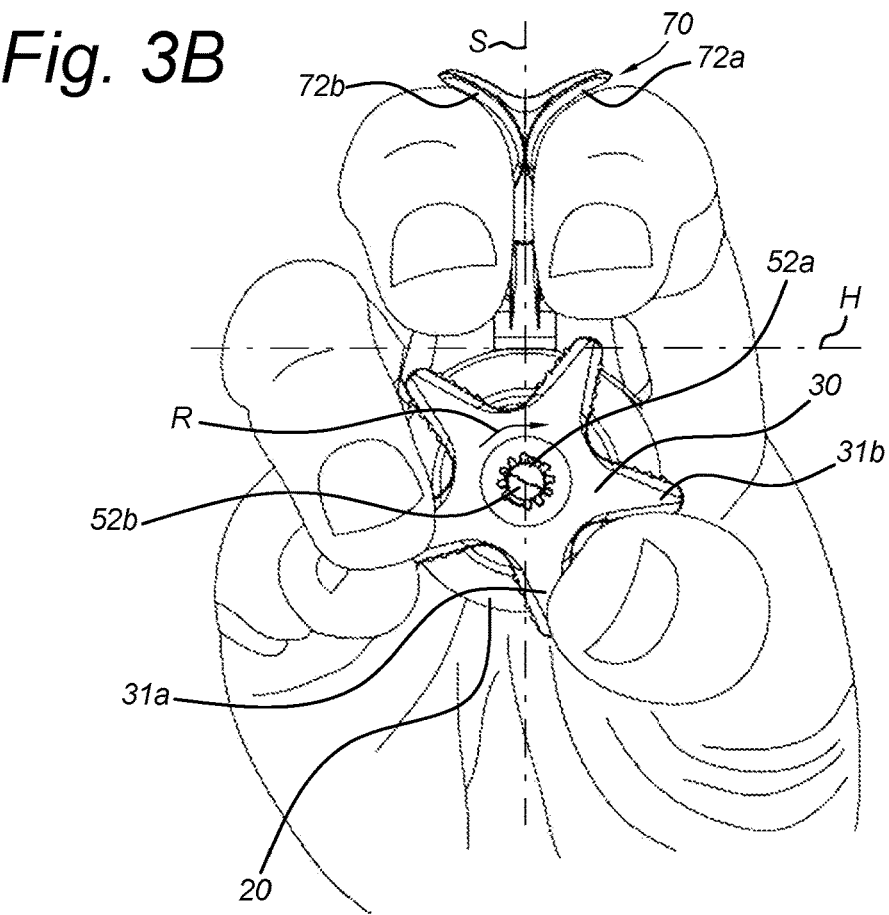

The present invention will be discussed in more detail below, with reference to the attached drawings, in which FIGS. 1A and 1B respectively schematically show a perspective view of a surgical instrument according to the invention with the distal tool in a closed state and in an open state;

FIG. 2 shows a cross-sectional view of the surgical instrument of FIG. 1A;

FIGS. 3A and 3B each show a front view of the surgical instrument of FIG. 1A, illustrating how a user operable rotation control thereof may be operated by a user holding the handle in single-handed grip;

FIGS. 4A-4D show the instrument of FIG. 1A, with the handle held by a user in different manners in a single handed grip.

DESCRIPTION OF EMBODIMENTS

FIG. 1A schematically shows a perspective view of a surgical instrument 1 according to the invention. The instrument has a handle 10 with a main body 20 which has a central axis C. A tubular body 40 having a substantially rigid main portion 41 extends from the handle 10. The tubular body, at an end 42 of the main portion 41 away from the handle, further comprises a bendable portion 43 and at a distal end 44 of the tubular body 40 is provided with a distal tool 50. Instead of a tubular body with bendable portion it is also conceivable that the entire tubular body is substantially rigid, though not shown in FIG. 1A. Typically, when the user holds the main body in a single handed grip, the central axis C will intersect the users hand palm, and the main body will be supported by at least the user's thumb and two or more fingers of the same hand. Two of those fingers may rest on finger abutment section 70 of a lever 60. The lever 60 is pivotable around pivot axis H, which extends spaced apart from and normal to the central axis C of the main body 20 and is fixed with respect to the main body. Using his fingers, the user can operate the lever 60 to mechanically actuate the distal tool 50. In FIG. 1A, the lever is in a closed position, in which the finger abutment section 70 is at a first distance from the central axis C, and in which correspondingly gripper arms 52a,52b of the distal tool 50 are in a closed position. FIG. 1B shows the lever in an open position in which the finger abutment section 70 is at a second distance from the central axis C, which second distance is greater than the first distance. With the lever in the open position, the gripper arms 52a,52b of the distal tool are in a corresponding open position.

For providing an ergonomic grip of the lever, the finger abutment section comprises a lower finger rest 71a,71b, an upper finger rest 72a,72b. The lower and upper finger rests are partitioned into a first and second finger receiving portion by a septum 73 which has a central plane which extends substantially parallel to the central axis C of the main body 20. The lower finger rest 71a,71b has a surface for contacting the ventral sides of a user's fingers, and has a convexly curved shape. The lever 60, from its portion 61 (see FIG. 2) that is arranged within the main body 20, to the distal end of the finger abutment section 70, in particular to the distal ends of the upper and lower finger rest thereof, spans an angle of at least 80 degrees when seen in cross-section through the central plane S.

Besides the main body 20, the handle 10 further comprises a unitary user operable bending and rotational control 30, which is moveably connected to the main body 20. By actuating the unitary control 30, the user can control rotation of the tubular body 40 around longitudinal axis L of its main portion 41. The control 30 also allows the user to control bending of bendable portion 43 of the tubular body 40 relative to the main portion 41 thereof.

FIG. 2 shows a cross-sectional view of the surgical instrument of FIG. 1A, illustrating how the distal tool 50 can be mechanically actuated by operation of the lever 60. Besides the finger abutment section 70 which is arranged outside of the outer surface of the main body 20, the lever comprises a portion 61 that is arranged within the main body 20. At an end of portion 61 the lever is connected to a push rod 90, which extends through the unitary control 30 and tubular body 40 and is connected to the distal tool 50. Movement of the push rod relative to the main body 20 thus results in actuation of the distal tool 50. From a point intersected by the hinge axis to a distal end of the finger abutment section, the lever arcs over an angle of about 50 degrees.

The main portion 41 of the tubular body 40 is attached to the unitary body. A number of Bowden cables 91a,91b from the bendable portion 43 of the tubular body 40 and extends through the tubular body 40 and are fixed to the interior of the main body 20. The tubular body 40 does not extend up to the point of attachment where the cables 91a,91b are attached to the main body 20, so that upon bending of the unitary control relative to the main body, the cables are bent correspondingly. This in turn results in movement of the cables 91a,91b with respect to the main portion 41 of the tubular body, and a corresponding bending of the bendable portion 43.

FIGS. 3A and 3B show front views of the instrument of FIG. 1A, in which the handle is held in a single-handed grip by a user. The user's index and middle fingers rest on the finger abutment section, so that the distal tool 50 can be actuated by operating the lever 60 in order to open the gripper arms 52a,52b. The main body 20 is held between the index and middle finger and thumb. As shown in FIG. 3B, instrument allows the user considerable freedom in moving his thumb and ring and little finger, while still firmly holding the handle. This allowed the user to reach with his thumb over the main body 20 of the handle to engage arms 31a,31b of the five-pointed star-shaped unitary user operable control 30, and rotate the unitary control and in conjunction there-with the distal tool 50, relative to the main body. Besides the manner of gripping shown, other manners of single-handedly gripping the handle are conceivable as well. For instance, instead of rotating the unitary control 30 using his thumb and/or ring finger, the user could rotate the unitary user operable control using only his index and middle finger while these rest on the finger abutment section 70.

Figure 4A:
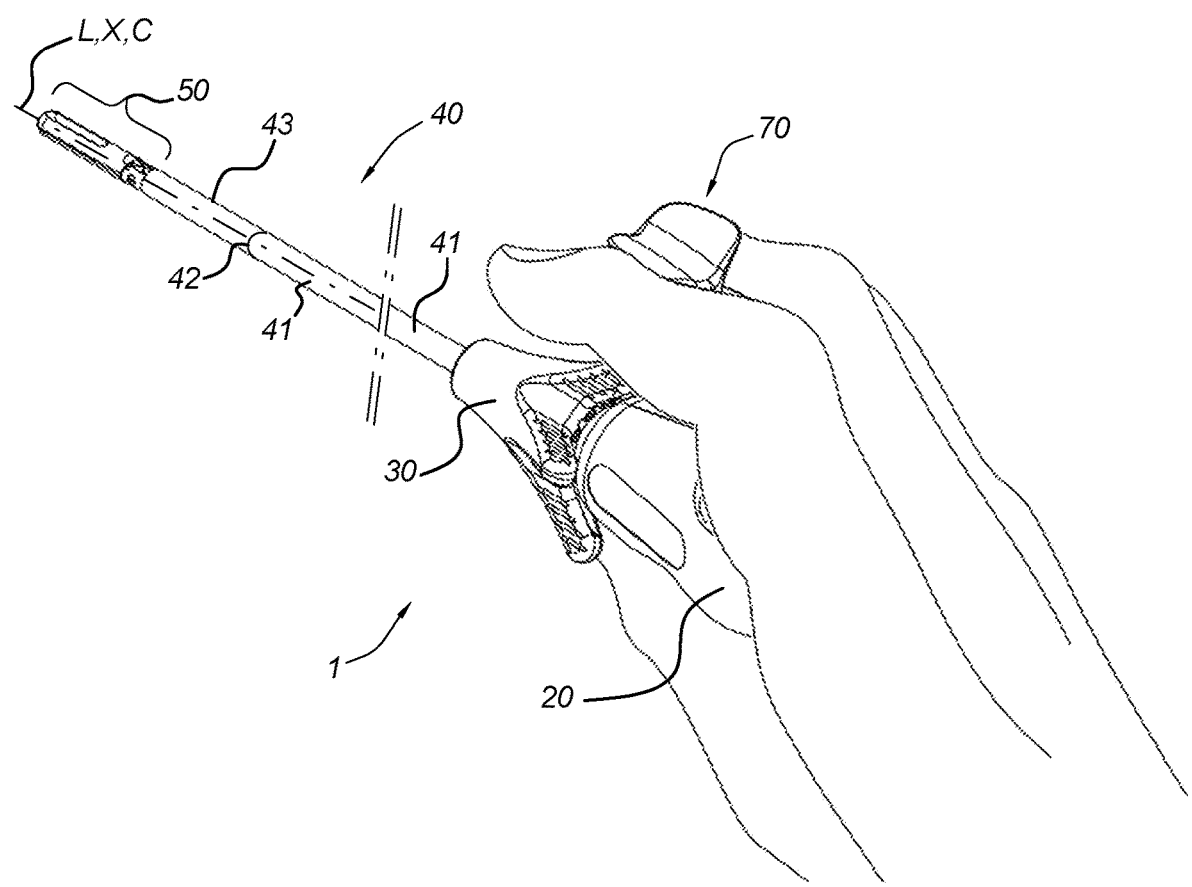

FIGS. 4A-4D show further examples of manners in which a user can grip the handle. FIG. 4A shows a user gipping the main body 20 between his thumb and his index and middle finger which rest on the finger abutment section. In FIG. 4A the finger abutment section 70 is in a closed position in which it lies at a first distance from the central axis C of the main body 20, and wherein the gripper arms of the distal tool 50, which is connected to the lever via a mechanical connection, are also in a closed position. The unitary user operable control 30 is moveably connected to the main body 20 such that the control can rotate around its central axis and/or bend relative to the main body 20. FIG. 4A shows the control 30 in a position in which the longitudinal axis X of the distal tool 50 substantially coincides with the longitudinal axis L of the main portion 41 of the tubular body 40.

Figure 4B:
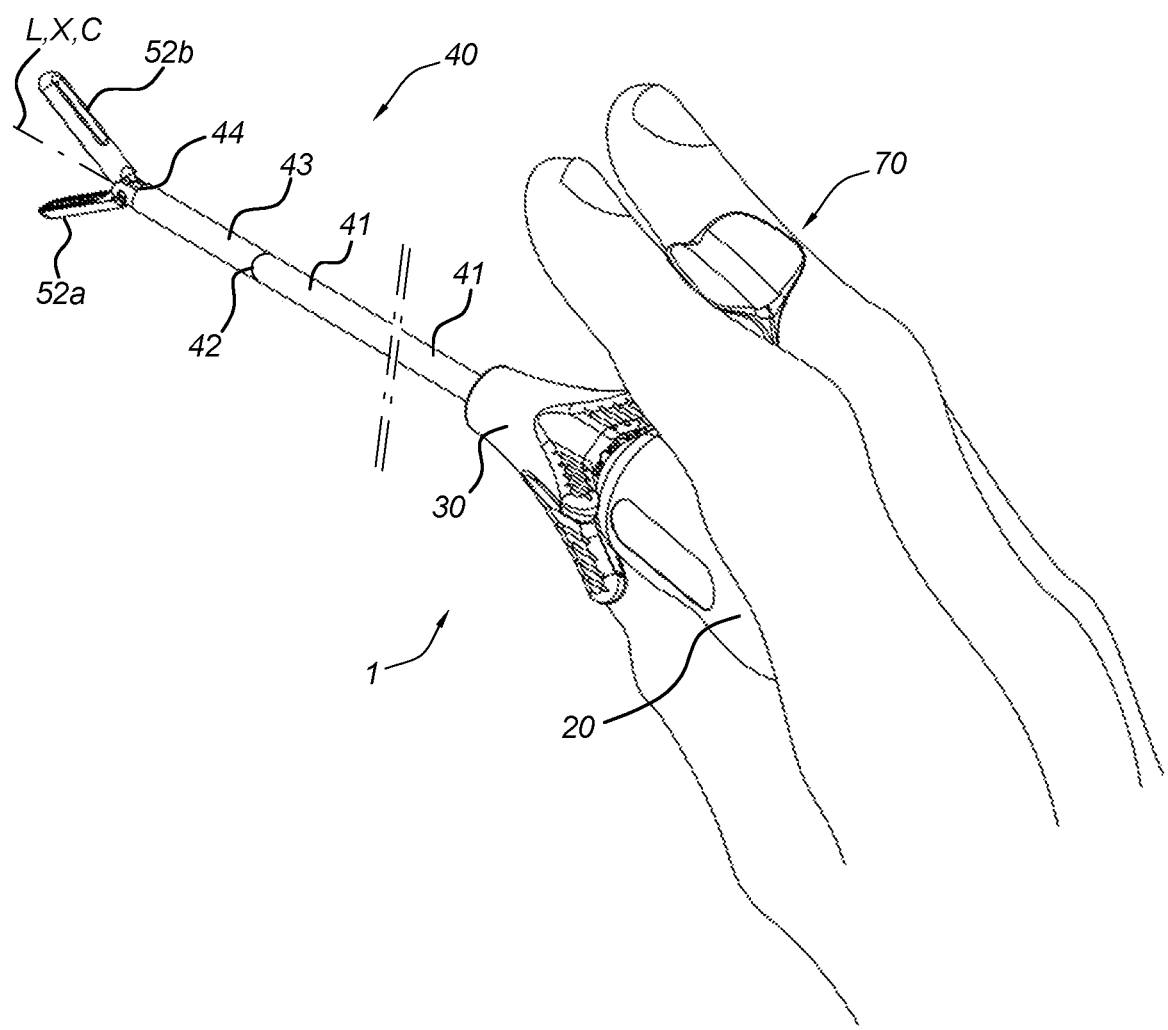

In FIG. 4B the user has substantially stretched his fingers to move the finger abutment surface to be at a second distance, greater than the first distance, from the central axis C. As a result, the gripper arms 52a,52b are actuated to an open position. Though the user's thumb may remain substantially in the same place on the outer surface of the main body 20 during movement of the lever, as shown in FIGS. 4A and 4B, this is not required. The user is substantially free to move his thumb about, and might even hold the main body 20 using four fingers while his thumb is not in contact with the main body 20, the user operable control 30 or other portion of the handle.

Figure 4C:
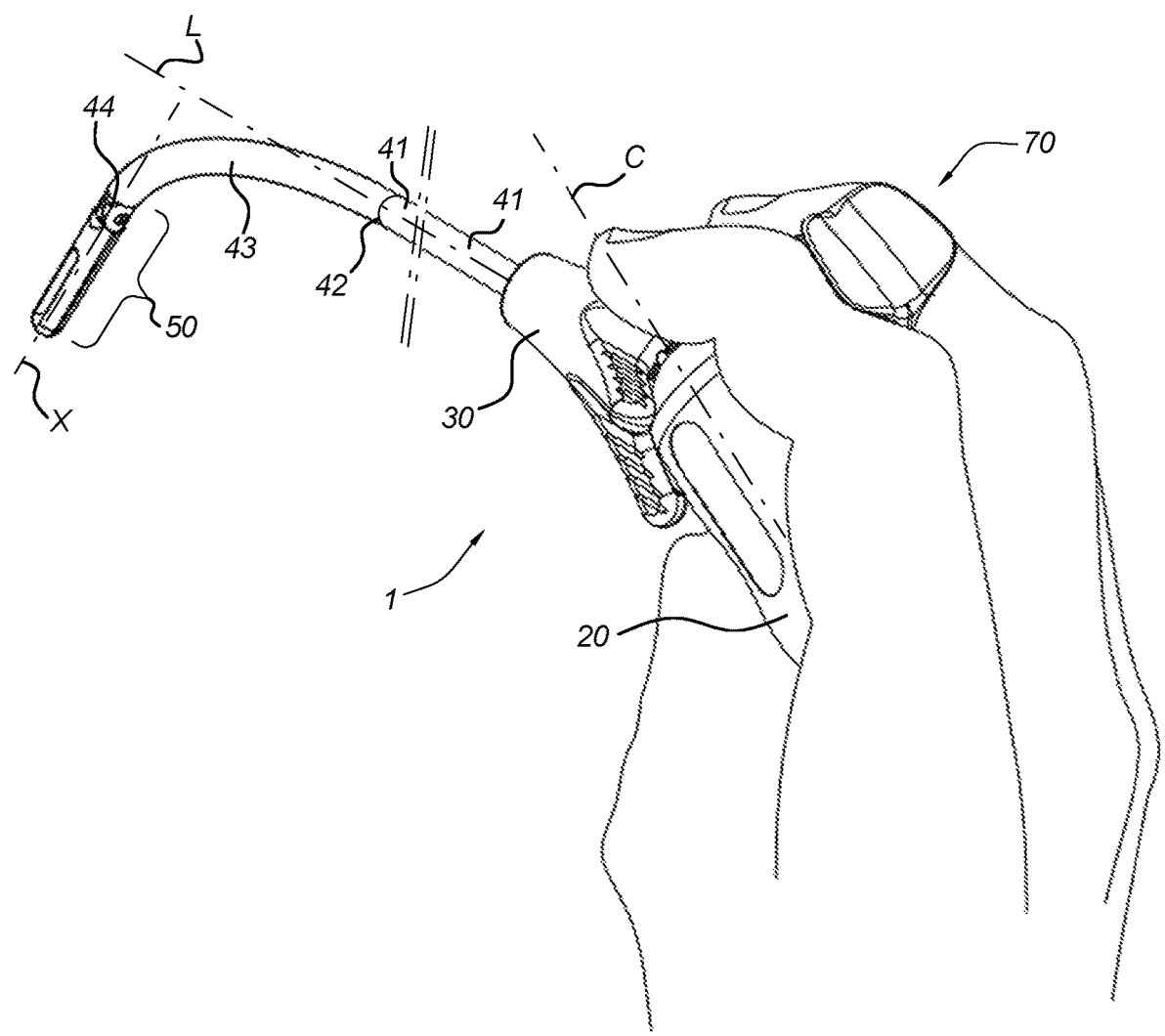
Figure 4D:
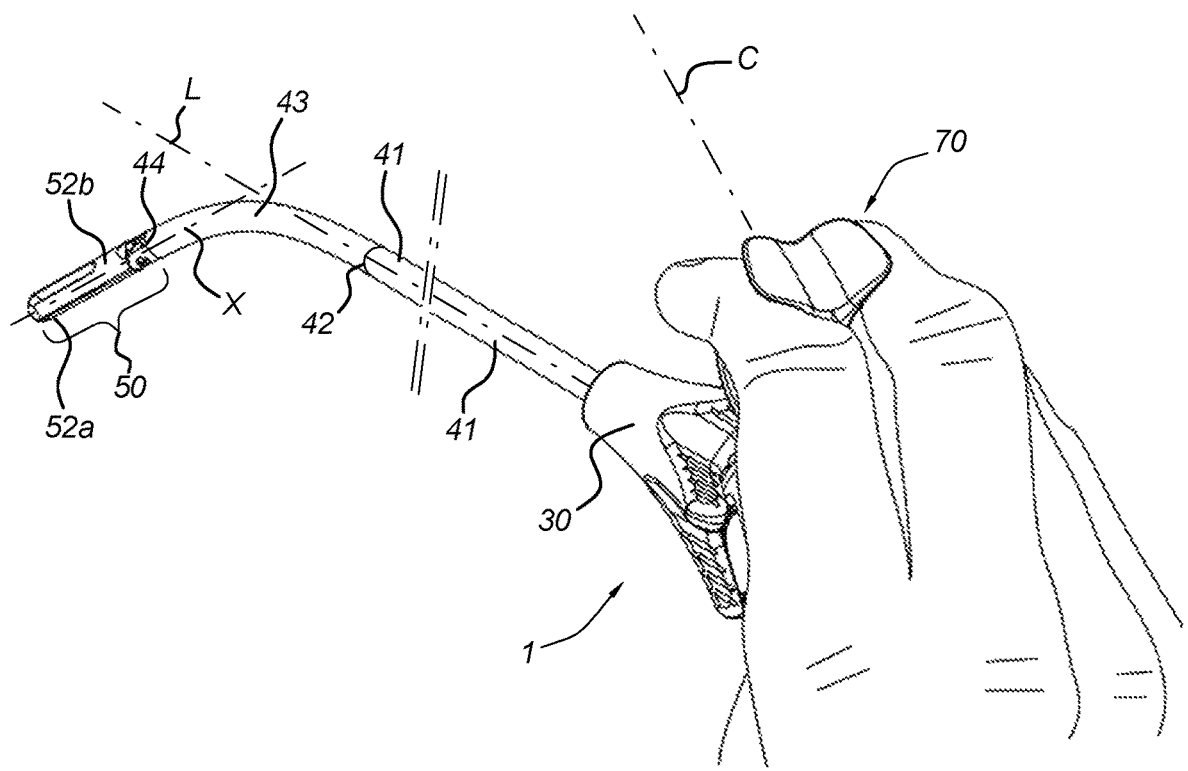

FIGS. 4C and 4D shows the instrument 1 with the user operable control 30 bend relative to the main body 20, to cause bending of the bendable portion 43 relative to the substantially rigid main portion 41 of the tubular body 40. In case the user wants to bend the bendable portion 43 relative to the main portion 41, he could hold the unitary user operable control between his thumb and little finger and/or ring finger, and move these relative to the main body to cause bending movement of the control 30 relative to the main body 20. Alternatively, the user can hold the finger abutment section 70 using his index finger and middle finger and cause movement of the main body 20 relative to the control 30 by exerting a force on the abutment section, e.g. in a direction out of or away from the central plane S. For causing rotation of the control 30 around its longitudinal axis, the user may simply move his thumb over the outer surface of the main body 20 to push against an arm of the star-shaped control 30 and drive rotation of the control 30 around its longitudinal axis.

In FIG. 4C the user has moved the user operable control 30 to a substantially downward direction relative to the main body 20. As a result, the bendable portion 43 is bent, so that the longitudinal axis X of the distal tool 50 is at an angle to the longitudinal axis L of the main portion 41 of the tubular body 40. As shown in FIG. 4C, the user's index and middle finger have reached over the finger abutment section 70 to contact the user operable control 30 and push it in a down bend relative to the main body 20. The user's thumb does not contact the user operable control, but does directly support the outer surface of the main body 20.

By changing the bending plane of the user operable control 30 relative to the main body and/or a degree of bending in said plane, a corresponding change in bending plane and/or degree of bending of the distal tool 50 relative to the main portion 41 of the tubular section may be achieved without rotating the main portion 41 around its longitudinal axis L. In order to rotate the main portion 41 around its longitudinal axis L with respect to the main body 20, the user can rotate the unitary user operable control around said longitudinal axis L using his thumb and/or fingers.

FIG. 4D shows the user holding the handle of the instrument in a slightly different grip. Here, the user's index and middle finger do not contact with the user operable control 30, nor does the user's thumb. Instead the user's ring and little finger push against the control 30 to bend it relative to the main axis C of the main body 20. It will be appreciated that many other ways of gripping and controlling the handle of the instrument according to the invention are possible. The instrument thus allows a user considerable freedom in choosing and/or varying a grip with which to hold the handle. This provides a significant ergonomical advantage, especially during long surgical procedures which may last for hours.

In summary, the invention relates to a surgical instrument comprising a handle with a main body having a central axis, a lever pivotable around a pivot axis that is fixed with respect to the main body, wherein the lever is provided with a finger abutment section comprising a lower finger rest adapted for at least partially contacting the ventral sides of both a first and second finger of a user during pivoting movement of said finger abutment section towards the central axis, and an upper finger rest adapted for at least partially contacting the dorsal sides of both said fingers during pivoting movement of the finger abutment section away from the central axis; and a septum fixed to the lower and upper finger rest and extending therebetween to form a separate first and second finger receiving portion for respectively receiving a first and a second finger of the user; wherein the lever is arranged for pivoting around the pivot axis in such a manner that during pivoting of the lever, a central plane of the septum remains substantially coplanar with a plane parallel to the central axis.

The present invention has been described above with reference to a number of exemplary embodiments as shown in the drawings. Modifications and alternative implementations of some parts or elements are possible, and are included in the scope of protection as defined in the appended claims. For instance, though the exemplary figures show a unitary user operable control, it is conceivable that a control having a similar outer appearance functions only as either a user operable bending control or a user operable rotation control. In case the surgical instrument is provided without a user operable bending and/or rotational control, it is preferred that the main portion of the tubular body is directly attached to the main body of the handle.

The present invention has been described above with reference to a number of exemplary embodiments as shown in the drawings. Modifications and alternative implementations of some parts or elements are possible, and are included in the scope of protection as defined in the appended claims. For instance, though the exemplary figures show a unitary user operable control, it is conceivable that a control having a similar outer appearance functions only as either a user operable bending control or a user operable rotation control. In case the surgical instrument is provided without a user operable bending and/or rotational control, it is preferred that the main portion of the tubular body is directly attached to the main body of the handle.

The invention claimed is:

1. A surgical instrument (1) comprising:
a handle (10) having a main body (20) with a central axis (C);
a tubular body (40) having a main portion (41) extending from the handle and a distal end (44) remote from the handle (10);
a distal tool (50), provided at the distal end (44) of the tubular body away from the handle;
a lever (60) pivotably attached to the main body (20) and operable by a user's fingers for mechanically actuating the distal tool (50), the lever being pivotable relative to the main body (20) about a pivot axis (H) substantially normal to the central axis (C), the lever having a finger abutment section (70), wherein the finger abutment section comprises a lower finger rest (71a,71b), an upper finger rest (72a,72b) and a septum (73) fixed to the lower and upper finger rest and extending therebetween to form a separate first and second finger receiving portion for respectively receiving a first and a second finger of the user,
wherein the lower finger rest is adapted for at least partially contacting the ventral sides of both the first and second finger during pivoting movement of said finger abutment section (70) towards the central axis (C), and wherein the upper finger rest is adapted for at least partially contacting the dorsal sides of both said fingers during pivoting movement of the finger abutment section (70) away from the central axis (C),
wherein the septum (73) has a central plane (S), wherein a first abutment surface of the septum is arranged on a first side of said plane and adapted for abutting a lateral side of a portion of the first finger of the user's hand in the first finger receiving portion, and wherein a second abutment surface of the septum is arranged on an oppositely facing second side of said plane (S) and adapted for abutting a lateral side of a portion of the second finger of said hand at the same time,
wherein the pivot axis (H) is fixed with respect to the main body (20) and wherein the lever is arranged for pivoting around the pivot axis (H) in such a manner that during pivoting of the lever the central plane of the septum (S) remains substantially coplanar with a plane parallel to the central axis (C),
wherein the handle is provided with a user operable rotation control (30) that is rotatably connected to the main body and fixed to the tubular body in such a manner that rotation of the user operable rotation control relative to the main body causes a corresponding rotation of the tubular body,
wherein the distal end (44) of the tubular body is adapted for bending relative to the main portion (41) of the tubular body, wherein the handle is provided with a user operable bending control (30) adapted for bending relative to the main body of the handle to mechanically cause bending of the distal tool relative to the distal end of the tubular body, and
wherein the user operable rotation control and the user operable bending control together form a unitary user operable control (30) that is rotatable and bendable relative to the main body (20) of the handle.

2. The surgical instrument according claim 1, wherein the finger abutment section (70) of the lever is arranged outside of the main body (20), wherein the lever (60) further comprises a portion (61) arranged within the main body of the handle, wherein said lever portion is connected to the distal tool (50) by means of a mechanical link which extends at least partially through the tubular body (40).

3. The surgical instrument according to claim 1, wherein the user operable rotation control partially surrounds an end of the main body, wherein the user operable rotation control, when seen in cross-section through a plane normal to a central axis, has a substantially star-shaped contour, wherein the outer points of the star shape are sufficiently spaced apart from each other and from the inner points of the star shape, for receiving a portion of a user's finger between adjacent points.

4. The surgical instrument according to claim 1, wherein a portion of the user operable rotation control that is fixed to the tubular body is arranged between the tubular body and the main body of the handle, and wherein the user operable rotation control has an outer surface arranged in such a manner relative to the finger abutment section and the main body of the handle as to enable a user holding the main body and having one or two fingers in the finger receiving portions to rotate the user operable control around its central axis by moving the outer surface relative to the main body.

5. The surgical instrument according to claim 1, wherein, when viewed in projection onto the central plane of the septum, the surface of the lower finger rest for contacting the ventral sides of the fingers extends over a first length of at least 2.0 cm, and wherein the upper finger rest extends over a second length of between 1.0 cm and 2.5 cm.

6. The surgical instrument according to claim 5, wherein the contacting surface is a substantially convexly curved surface.

7. The surgical instrument according to claim 6, wherein said curved surface, when projected onto the central plane (S), substantially corresponds to a segment of an ellipse, having a first diameter in the range of 15 and 21 cm, and a second diameter in the range of 23 cm and 29 cm.

8. The surgical instrument according to claim 1, wherein each of the finger receiving portions is adapted for allowing the user to move his finger into and out of the finger receiving portion in a direction substantially normal to the central plane (S) of the septum.

9. The surgical instrument according to claim 1, wherein each of the finger receiving portions is open ended at a side thereof opposite from the septum.

10. The surgical instrument according to claim 1, wherein the main body (20) and the finger abutment section (70) together are adapted for being held in a one-handed pincer-grip.

11. The surgical instrument according to claim 1, wherein the lower finger rest comprises a first portion (71*a*) for contacting the ventral side of the first finger and a second portion (71*b*) for contacting the ventral side of the second finger, wherein the upper finger rest comprises a first portion (72*a*) for contacting the dorsal side of the first finger and a second portion (72*b*) for contacting the dorsal side of the second finger, wherein the first portions (71*a*,72*a*) of the upper finger rest and the lower finger rest face each other and a distance between said portions (71*a*,72*a*) is in the range of 1.5 to 3 cm, and wherein the second portions (71*b*,72*b*) of the upper finger rest and the lower finger rest face each other and a distance between said portions (71*b*,72*b*) is in the range of 1.5 to 3 cm.

12. The surgical instrument according to claim 1, wherein, when seen in projection onto a plane normal to the central plane (S) of the septum, the lower finger rest (71*a*,71*b*) completely overlaps the upper finger rest (72*a*,72*b*).

13. The surgical instrument according to claim 1, wherein, when seen in projection onto the central plane (S) of the septum, the lower finger rest (51) is spaced apart from the upper finger rest (52) by at least 1.5 cm.

14. The surgical instrument according to claim 1, wherein the main portion of the tubular body is substantially rigid.

15. The surgical instrument according to claim 1, wherein the lever arcs over an angle of at least 80 degrees when viewed in cross-section through the central plane (S).

16. The surgical instrument according to claim 1, wherein the distal tool comprises a cutter, a gripper and/or a manipulator.

17. The surgical instrument according to claim 1, wherein the lever is movable with respect to the handle between an open and a closed position, wherein the lever is not biased to the open position nor to the closed position.

18. The surgical instrument according to claim 1, wherein the main body (20) and the finger abutment section (70) together are adapted for being held in a one-handed pincer-grip, in which the central axis intersects the hand palm of said hand.

19. The surgical instrument according to claim 1, wherein, when viewed in projection onto the central plane of the septum, the surface of the lower finger rest for contacting the ventral sides of the fingers extends over a first length of at least 4 cm and wherein the upper finger rest extends over a second length of between 1.0 cm and 2.5 cm.

20. The surgical instrument according to claim 1, wherein each of the finger receiving portions is open ended at a side thereof opposite from the septum, wherein the finger abutment section (70), when seen in cross-section through a plane normal to the central plane (S) of the septum, has a substantially H-shaped contour.

\* \* \* \* \*